US012642454B1

(12) United States Patent
Wang et al.

(10) Patent No.: US 12,642,454 B1
(45) Date of Patent: Jun. 2, 2026

(54) WEARABLE TRIBOELECTRIC SENSORS FOR MONITORING BODILY MOTIONS

(71) Applicants: Gang Wang, Madison, AL (US); Moonhyung Jang, Madison, AL (US)

(72) Inventors: Gang Wang, Madison, AL (US); Moonhyung Jang, Madison, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 378 days.

(21) Appl. No.: 18/517,609

(22) Filed: Nov. 22, 2023

Related U.S. Application Data

(60) Provisional application No. 63/489,618, filed on Mar. 10, 2023, provisional application No. 63/384,774, filed on Nov. 22, 2022.

(51) Int. Cl.
*A61B 5/11* (2006.01)
*A61B 5/00* (2006.01)
(52) U.S. Cl.
CPC .............. *A61B 5/1126* (2013.01); *A61B 5/72* (2013.01)
(58) Field of Classification Search
None
See application file for complete search history.

(56) References Cited

U.S. PATENT DOCUMENTS

| | | | |
|---|---|---|---|
| 11,929,691 | B1 | 3/2024 | Wang et al. |
| 2011/0050181 | A1 | 3/2011 | Post et al. |
| 2013/0049531 | A1 | 2/2013 | Wang et al. |
| 2017/0331397 | A1 | 11/2017 | Kim et al. |
| 2017/0359001 | A1 | 12/2017 | Wang et al. |

FOREIGN PATENT DOCUMENTS

CN 111245285 6/2020

OTHER PUBLICATIONS

Jang et al. Self-powered triboelectric wearable biosensor using Scotch tape; J. Mater. Chem. B, 2023, 11, 10640. (Year: 2023).*

(Continued)

*Primary Examiner* — Jay B Shah
(74) *Attorney, Agent, or Firm* — Butler Snow LLP; Jon E. Holland

(57) ABSTRACT
A wearable triboelectric sensor has a first layer with surface charges at the same polarity and a second layer with both positive and negative surface charges. The two layers are held together by electrostatic forces generated by surface charges of opposite polarity. Electrostatic forces generated by surface charges of the same polarity force the layers away from each other causing gaps between the layers. When the sensor is placed on the skin of a user, bodily movements induce compressive and tensile stresses that force the layers toward and away from each other causing the gaps to close and open. Contact and separation of the two layers in the areas of the gaps induce a triboelectric voltage that can be measured to determine an extent of the bodily movement. Thus, the bodily movement can be accurately detected with a relatively small, inexpensive sensor that does not require an active power source.

22 Claims, 4 Drawing Sheets

(56) References Cited

OTHER PUBLICATIONS

Liu, et al., "Quantifying contact status and the air-breakdown model of charge-excitation nanogenerators to maximize charge density," Nature Communications, 2020, pp. 1-8.

Luo et al., "Recent progress of triboelectric nanogenerators: From fundamental theory to practical applications", EcoMat, vol. 2, No. 4, 2020, pp. 1-22.

Dong et al., "A Stretchable Yarn Embedded Triboelectric Nanogenerator as Electronic Skin for Biomechanical Energy Harvesting and Multifunctional Pressure Sensing", Advanced Materials., vol. 30, No. 43, 2018, pp. 1-12.

Wang et al., "Triboelectric nanogenerators as flexible power sources", npj Flexible Electronics, vol. 1, 2017, pp. 1-10.

Wang et al., "Achieving ultrahigh triboelectric charge density for efficient energy harvesting", Nature Communications, vol. 8, No. 1, 2017, pp. 1-8.

Liu et al., "Integrated charge excitation triboelectric nanogenerator", Nature Communications, vol. 10, No. 1, 2019, pp. 1-9.

Wang et al., "Pumping up the charge density of a triboelectric nanogenerator by charge-shuttling", Nature Communications, vol. 11, No. 1, 2020, pp. 1-9.

Camara et al., "Correlation between nanosecond X-ray flashes and stick-slip friction in peeling tape", Nature, vol. 455, No. 7216,2008, pp. 1089-1092.

* cited by examiner

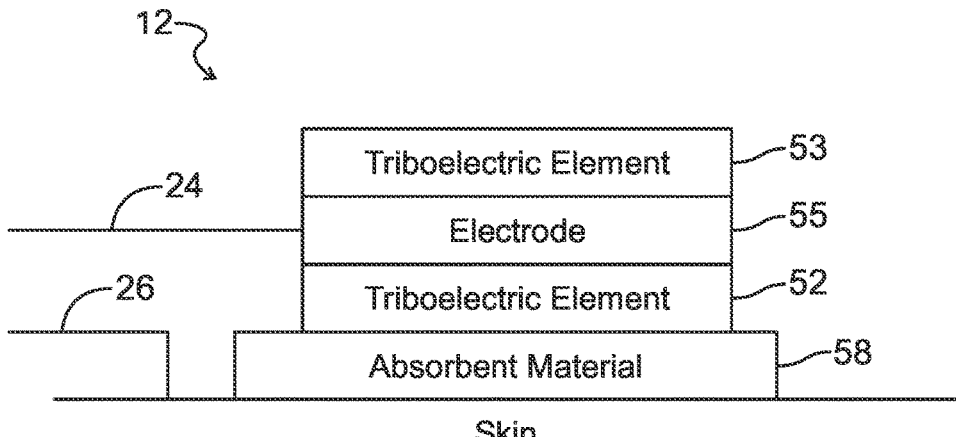
FIG. 3
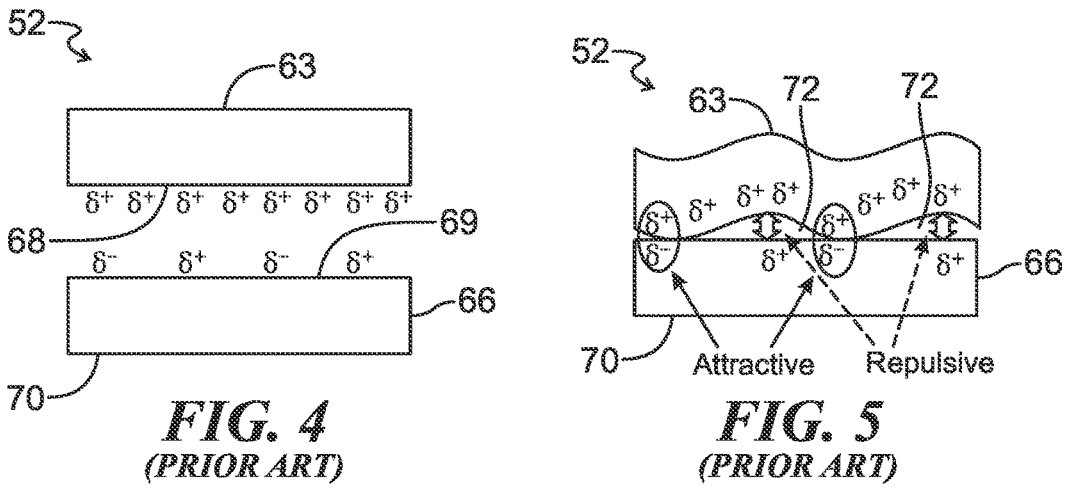
FIG. 4
*(PRIOR ART)*
FIG. 5
*(PRIOR ART)*
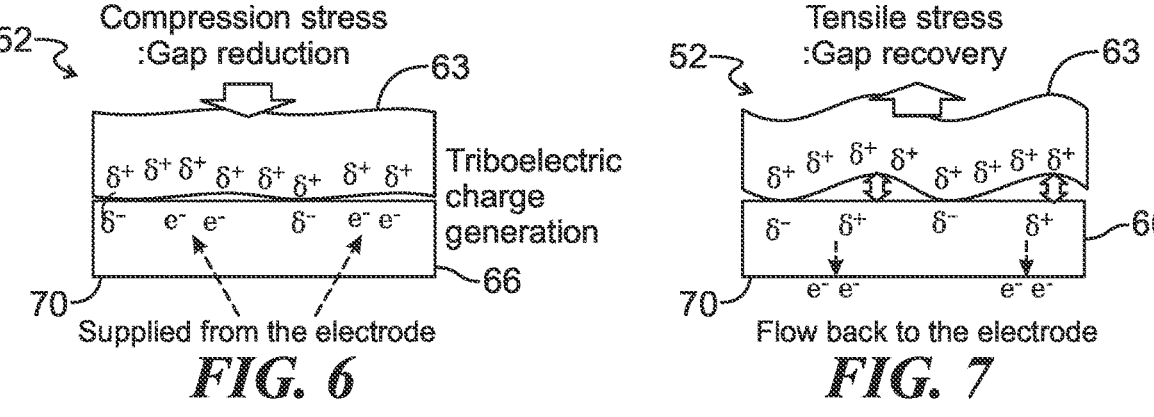
FIG. 6
FIG. 7

WEARABLE TRIBOELECTRIC SENSORS FOR MONITORING BODILY MOTIONS

CROSS REFERENCE TO RELATED APPLICATION

This application claims priority to U.S. Provisional Patent Application No. 63/384,774, entitled "Wearable Triboelectric Sensor for Motion Monitoring" and filed on Nov. 22, 2022, which is incorporated herein by reference. This application also claims priority to U.S. Provisional Patent Application No. 63/489,618, entitled "Powerless Wearable Triboelectric Biosensor for Human Body Monitoring" and filed on Mar. 10, 2023.

RELATED ART

Electromyography (EMG) sensors have been used to detect electrical activity induced by skeletal muscles. Such EMG sensors often operate by detecting electrical energy on the surface of a user's skin, and such information may be used to infer or otherwise determine muscle movement. In this regard, when a muscle contracts, it generates a burst of electrical energy that passes through the body. An EMG sensor often has electrodes that are positioned on the user's skin to detect such energy at the skin surface. In general, a greater amount of electrical energy detected generally indicates greater muscle movement such that the detected energy can be used to estimate of an amount of muscle movement.

EMG sensors are often bulky and expensive. In addition, EMG sensors and other wearable devices for sensing body motion often require a power source, which can make continuous monitoring over long periods of time challenging. Using a battery can make a sensor bulkier and more expensive and also limit the useful life of the sensor. Improved techniques for monitoring muscle movement and other types of motions using less invasive and less expensive sensors are generally desirable. It is further desirable for such sensors to be capable of continuous monitoring over long periods of time.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 3 a side view illustrating an embodiment of a wearable triboelectric sensor, such as is depicted by FIG. 1.

FIG. 4 is a side view illustrating an embodiment of a triboelectric element, such as is depicted by FIG. 3, having two layers before the layers are joined during manufacturing.

FIG. 5 is a side view illustrating the layers of FIG. 4 after the layers have been joined.

FIG. 6 is a side view illustrating the layers of FIG. 5 after a compressive stress has been applied to the layers causing gaps between the layers to close at least partially.

FIG. 7 is a side view illustrating the layers of FIG. 5 after a tensile stress has been applied to the layers causing gaps between the layers to open.

DETAILED DESCRIPTION

The present disclosure generally pertains to wearable triboelectric sensors for monitoring bodily motions. A wearable triboelectric sensor in accordance with some embodiments of the present disclosure has at least two layers. One layer has surface charges substantially at the same polarity (e.g., either positive or negative), and the other layer has a surface with both positive and negative charges dispersed across the surface in a random manner. During manufacturing, the surfaces of the two layers are placed into contact with each or otherwise positioned sufficiently close such that the two layers are held together by electrostatic forces generated by charges of opposite polarity on the surfaces of the layers. Electrostatic forces generated by charges of the same polarity at the surfaces of the two layers tend to force the layers away from each other causing gaps between the layers. When the sensor is placed on the skin of a user, bodily movements (e.g., muscle movements or joint movements) induce compressive and tensile stresses that tend to force the layers toward and away from each other causing the gaps to close and open. Contact and separation of the two layers in the areas of the gaps induce a triboelectric voltage that can be measured to determine an extent of the bodily movement. Thus, the bodily movement can be accurately detected with a relatively small, inexpensive sensor that does not require an active power source.

Figure 1:
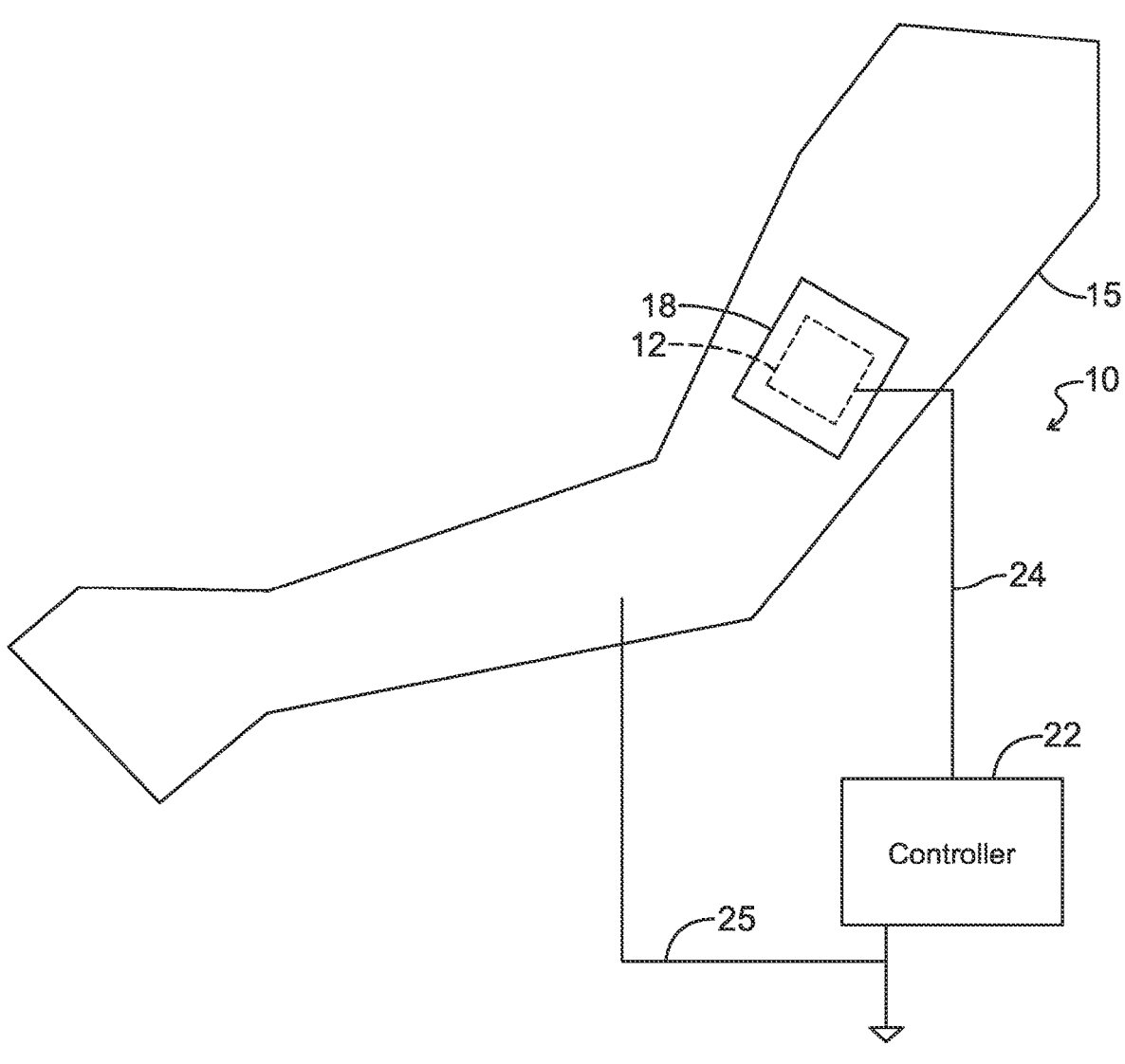
FIG. 1 depicts an embodiment of a triboelectric monitoring system for measuring bodily motion using a wearable triboelectric sensor.

FIG. 1 depicts an exemplary embodiment of a triboelectric monitoring system 10 having a wearable triboelectric sensor 12 for detecting bodily motions. In the embodiment depicted by FIG. 1, the triboelectric sensor 12 is secured to an arm 15 of a user by a covering 18 that hides the triboelectric sensor 12 from view. The exemplary covering 18 may be medical tape or other type of tape, but other types of devices and techniques for securing the triboelectric sensor 12 to a body part are possible.

As shown by FIG. 1, the triboelectric sensor 12 is coupled to a controller 22 by a wire 24 comprising a conductive core (not specifically shown). In some embodiments, a ground plane of the controller 22 is coupled by a wire 25 to the user, such as the same body part (e.g., arm) to which the triboelectric sensor 12 is secured.

As will be described in more detail below, the triboelectric sensor 12 is attached to skin of the user and is configured to generate a small amount of triboelectric current in response to skin movement, such as skin movement caused by muscle motion (e.g., muscle flexes) or joint movement (e.g., bending of an arm at an elbow or a leg at a knee). In the embodiment depicted by FIG. 1, the triboelectric sensor 12 is positioned on the user's skin at the location of the user's bicep in order to measure movement (e.g., flexes) of the bicep. However, the triboelectric sensor 12 may be placed at other locations. As an example, the triboelectric sensor 12 may be placed on the skin at other muscles to sense movement of such muscles. The triboelectric sensor 12 may also be placed on the user's skin at a joint, such as a knuckle, knee, ankle, or elbow, to sense bending or other type of motion of the joint or body parts connected to the joint.

The controller 22 is configured to capture and store samples of measurements by the triboelectric sensor 12 and to analyze the samples to determine values indicative of the motion of one or more body parts, such as a muscle or joint. In the embodiment, shown by FIG. 1, the controller 22 is configured to use motion sensed by the triboelectric sensor 12 to determine values indicating an extent to which the bicep moves (e.g., flexes) over time. In this regard, the triboelectric sensor 12 is configured to continuously provide a voltage indicating an extent that the user's skin is moving. Specifically, greater movement of the user's skin causes the triboelectric sensor 12 to generate greater current resulting in an increase in voltage. By monitoring the voltage over time, the controller 22 can determine and record movement of the user's muscle that induced the skin movements detected by the triboelectric sensor 12.

Figure 2:
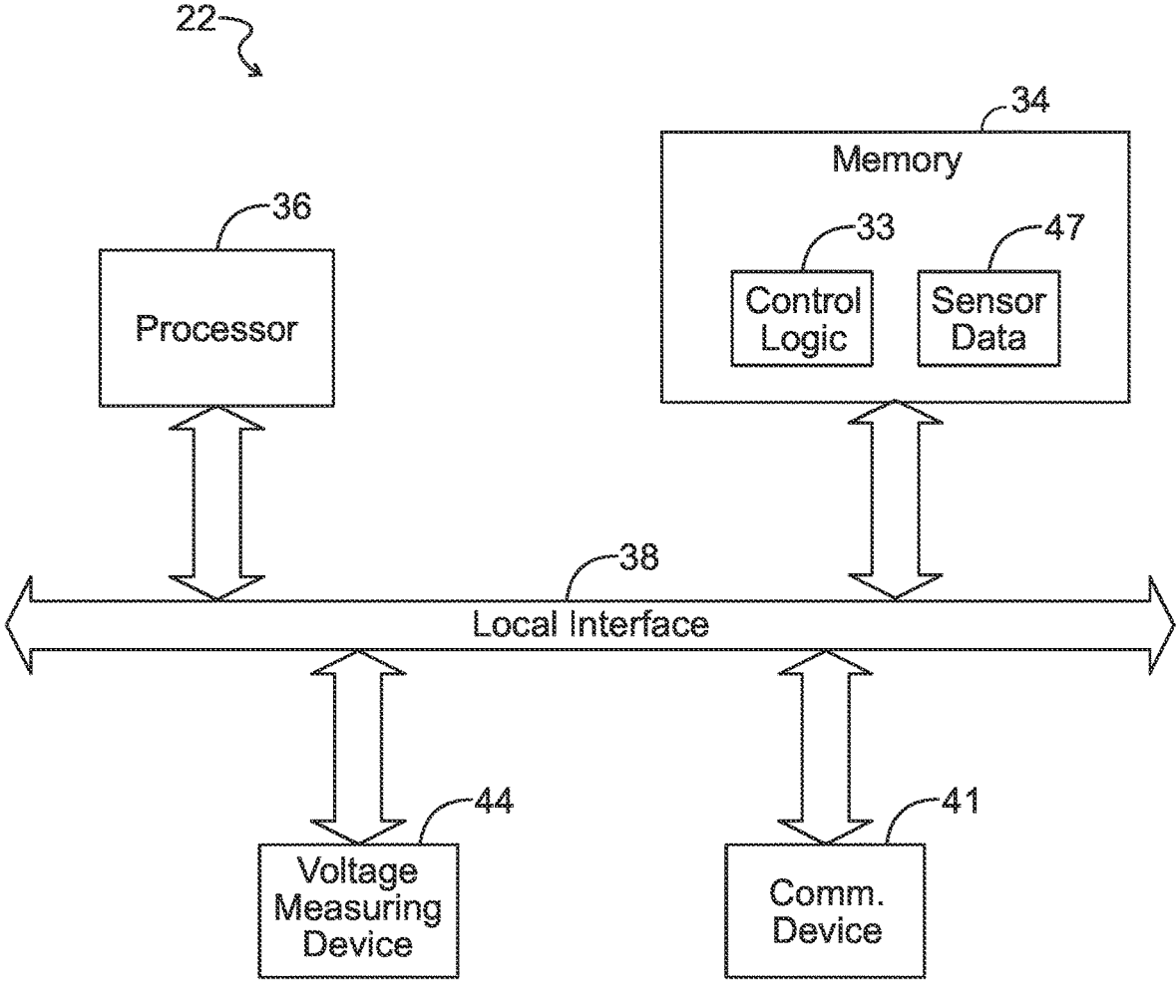
FIG. 2 is a block diagram illustrating an embodiment of a controller for a triboelectric monitoring system, such as is depicted by FIG. 1.

FIG. 2 depicts an exemplary embodiment of the controller 22. As shown by FIG. 2, the controller 22 comprises control logic 33 for generally controlling the operation of the controller 22, as will be described in more detail hereafter. The control logic 33 can be implemented in software, hardware, firmware or any combination thereof. In the exemplary controller 22 illustrated by FIG. 2, the control logic 33 is implemented in software and stored in memory 34 of the controller 22.

Note that the control logic 33, when implemented in software, can be stored and transported on any computer-readable medium for use by or in connection with an instruction execution apparatus that can fetch and execute instructions. In the context of this document, a "computer-readable medium" can be any means that can contain or store a computer program for use by or in connection with an instruction execution apparatus.

The exemplary controller 22 depicted by FIG. 2 comprises at least one conventional processor 36, such as a digital signal processor (DSP) or a central processing unit (CPU), that communicates to and drives the other elements within the controller 22 via a local interface 38, which can include at least one bus. As an example, the processor 36 may be implemented with a conventional microprocessor that is configured to retrieve and execute instructions stored in memory 34. In some embodiments, the controller 22 has a communication device 41, such as a modem, radio frequency (RF) transceiver, or other type of communication device, that enables the controller 22 to communicate with external devices or systems. As an example, the communication device 41 may communicate with a network (e.g., a cellular network or the Internet) to transmit information about body movements determined by the controller 22. In some embodiments, the communication device 41 may communicate via a short-range protocol, such as Bluetooth, near field communication (NFC), or radio frequency identification (RFID). Yet other configurations of the communication device 41 are possible in other embodiments.

As shown by FIG. 2, the controller 22 also has a voltage measuring device 44, such as an oscilloscope or voltmeter, for determining a voltage of the sensor signal provided by the triboelectric sensor 12. Information indicative of the measured voltages may be stored in memory 34 and referred to hereafter as "sensor data 47." Note that the controller 22 or at least components of the controller 22 may be attached to or carried by the user. As an example, the controller 22 may be secured to a body part or clothing (e.g., belt or shirt) of the user. In some embodiments, the voltage sensing device 44 and the communication device 41 are integrated with the triboelectric sensor 12 or otherwise located at the location of the triboelectric sensor 12 and provide sensor data 47 to the control logic 33. For example, the control logic 33 may be implemented as an application or "app" on a smartphone (or other mobile device) carried by the user, and the smartphone may receive the sensor data via Bluetooth or other short-range communication protocol. Various other configurations of the controller 22 are possible in other embodiments.

FIG. 3 depicts an exemplary embodiment of the triboelectric sensor 12. As shown by FIG. 3, the triboelectric sensor 12 has at least one triboelectric element 52, 53 that is configured to generate current through triboelectric charging, as will be described in more detail below. The exemplary triboelectric sensor 12 shown by FIG. 3 has two triboelectric elements 52, 53, but there may be any number (e.g., one or more) of triboelectric elements in other embodiments.

In the embodiment shown by FIG. 3, an electrode 55 is positioned between and in contact with the triboelectric elements 52, 53. The electrode 55 is composed of a conductive material, such as aluminum or copper, and is coupled to the controller 22 via the wire 24. In some embodiments, the end of the wire 24 (e.g., an exposed end of the conductive core of the wire 24) may form the electrode 55 or the conductive core of the wire 24 may be soldered or otherwise attached to conductive material forming the electrode 55.

The embodiment of FIG. 3 also shows absorbent material 58 positioned between the triboelectric element 52 and the user's skin. The absorbent material 58 absorbs moisture, such as perspiration that may be emitted from the skin. It has been observed that using a conductive material 58 to absorb moisture on the surface of the user's skin helps to improve the quality of the sensor signal provided by the triboelectric sensor 12 (e.g., provide greater peak voltages). It is believed that absorbing moisture between the skin and the sensor 12 may help to reduce the effect of moisture on frictional forces thereby helping the triboelectric elements 52, 53 to experience greater compressive and tensile forces in response to skin movement. In one embodiment, a cotton gauze is used as the absorbent material 58, but other types of materials may be used in other embodiments, and it is possible to implement the triboelectric sensor 12 without using absorbent material 58 as described.

FIGS. 4-7 depict an exemplary embodiment of a triboelectric element 52. Note that the triboelectric element 53 may have the same configuration as the triboelectric element 52 shown by FIGS. 4-7. As shown by FIGS. 4-7, the triboelectric element 52 has two layers 63, 66 that are joined together during manufacturing. In this regard, FIG. 4 shows the two layers 63, 66 prior to being joined together. One layer 63 has surface charges at the same polarity (e.g., either positive or negative), and the other layer 66 has a surface with both positive and negative charges dispersed across the surface in a random manner. As an example, the layer 63 may be composed of polypropylene having positive charges distributed across the surface 68 of the layer 63 that is to contact the layer 66. The layer 66 may be acrylic having positive and negative charges distributed across its surface 69 in a random manner.

During manufacturing, the layer 63 is positioned such that its surface 66 contacts the surface 68 of the layer 66, as shown by FIG. 5. In areas for which positive surface charges of the layer 63 are close to negative surface charges of the layer 66, the charges generate electrostatic forces that tends to hold the layers 63, 66 together. That is, these electrostatic forces attract the layer 66 to the layer 63. However, in areas for which positive surface charges of the layer 63 are close to positive surface charges of the layer 66, the charges generate electrostatic forces that tend to push the layers 63, 66 away from each other. That is, these electrostatic forces repel the layer 66 from the layer 63. Thus, small gaps 72 form in areas for which positive surface charges of the layer 63 are close to negative surface charges of the layer 66, as shown by FIG. 5.

Note that conventional Scotch tape is composed of a polypropylene layer 63 in contact with an acrylic layer 66, as described above, and may be used to implement each the triboelectric elements 52, 53 described herein. For scotch tape, the surface 70 of layer 66 opposite of the surface 69 has adhesive material deposited or otherwise formed thereon to allow the surface 70 to stick to objects, as known in the art. In the embodiment depicted by FIG. 3, the sticky surface 70 of the layer 66 of triboelectric element 52 contacts and sticks to the absorbent material, and the layer sticky surface 70 of the layer 66 of the triboelectric element 53 contacts and sticks to the electrode 55.

Figure 8:
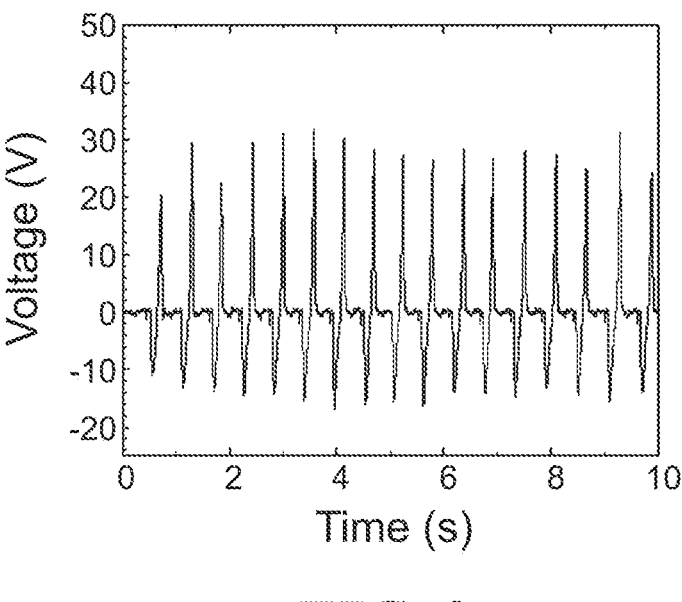
FIG. 8 is a graph illustrating voltage versus time for measurements from a triboelectric sensor, such as is depicted by FIG. 3.

When the triboelectric element 52 depicted by FIG. 5 undergoes compressive stress (e.g., due to skin movement that tends to force the layers 63, 66 together), the surface 68 is pressed against the surface 69 such that the gaps 72 close at least partially, as shown by FIG. 6. That is, the space formed by each gap 72 is reduced causing a greater overall area of the surface 68 to contact the surface 69. However, when triboelectric element 52 undergoes tensile stress (e.g., due to skin movement that tends to force the layers 63, 66 away from each other), the gaps 72 open, as shown by FIG. 7. That is, the space formed by each gap 72 is increased causing less overall area of the surface 68 to remain in contact with the surface 69. Changing of the stresses applied to the triboelectric element 52 causes portions of the surfaces 68, 69 to contact each other and separate as the gaps 72 close and open, thereby generating a triboelectric voltage that can be measured. In this regard, each triboelectric element 52, 53 is conductively coupled to the electrode 55 through which the triboelectric voltage generated by the triboelectric elements 52, 53 is measured by the controller 22. As an example, FIG. 8 shows exemplary voltage measurements by the controller 22 when the sensor 12 is positioned at a user's elbow while the user is repetitively bending and straightening his or her arm at the elbow. Each time the moves (e.g., bends or straightens) his or arm, a burst of voltage is generated shown as a pulse in FIG. 8. In general, a higher peak indicates greater arm movement.

Note that the triboelectric voltage described above is generated by the well-known phenomena of the triboelectric effect, which generally refers to the electric charge transfer that occurs when two objects contact each other. This charge transfer is sometimes referred to as "triboelectricity" or "tribocharge." When a gap 72 of a triboelectric element 52, 53 closes thereby allowing a greater surface area of the layer 63 to contact the layer 66, tribocharge is generated such that the triboelectric voltage measured by the controller 22 through the sensor 12 is increased. The measurements captured by the controller 22 via the sensor 12 can be analyzed over time to assess skin movements, which can be correlated with certain body motions, such as muscle flexes or joint bends, depending on the location of the sensor 12.

Various experiments have been performed using the sensor configuration shown by FIG. 3 where each triboelectric layer 52, 53 is implemented with a strip of conventional Scotch tape. It was found that optimal results (e.g., a relatively clean voltage signal with relatively high peak voltages) are achieved with the configuration of FIG. 3 when the triboelectric elements 52, 53 are oriented in the same direction. In this regard, as described above, the triboelectric element 52 is positioned such that the sticky surface 70 of the element 52 faces the user's skin and contacts the absorbent material 58 that is positioned between the triboelectric element 52 and the user's skin. Note that the user of the absorbent material 58 is unnecessary, and it is possible for the sticky surface 70 of the element 52 to contact the user's skin. In addition, the triboelectric element 53 is positioned such that the sticky surface 70 of the element 53 also faces the user's skin and contacts the electrode 55.

While the sensor configuration depicted by FIG. 3 has been shown to provide good results, it should be noted that other configurations of the sensor 12 are possible. As an example, it is possible to use a single triboelectric element 52 or 53 rather than multiple triboelectric elements, though the use of multiple triboelectric elements 52, 53, as shown by FIG. 3, provides greater voltages thereby improving the quality of the sensor signal. Also, it is possible for the orientations of the triboelectric layers 52, 53 to be different than what is described above. For example, experiments have shown that the sensor 12 is operational when the triboelectric element 52 is oriented upside down such that the sticky surface 70 of the element 52 faces and contacts the electrode 55 rather than facing the user's skin.

In operation, the triboelectric sensor 12 may be positioned on a user's skin, as shown by FIGS. 1 and 3. Note that the sensor 12 may be secured to the user's body by a covering 18 (e.g., medical tape) that extends over the sensor 12 and adheres to the user's skin, as shown by FIG. 1. In this regard, a surface of the covering 18 facing the sensor 12 and the user's skin may have an adhesive material deposited or otherwise formed thereon such that the covering 18 sticks to the sensor 12 and the user's skin, thereby pressing or otherwise holding the sensor 12 against the user's skin. In other embodiments, other techniques for securing the sensor 12 to the user's body are possible.

Body motions by the user, such as muscle flexes or bending of joints, cause skin movements that apply compressive and tensile stresses to the sensor 12. Changes in such stresses cause portions of the layers 63, 66 of each triboelectric element 52, 53 to come into contact and to separate thereby generating a triboelectric voltage that is continuously measured and recorded by the controller 22.

This voltage changes with skin movement such that the sensor 12 implements a biosensor for use in measuring bodily motion by the user. The controller 22 may be configured to analyze the measurements to determine information indicative of the body motions, such as the extent that user flexes a muscle or bends a joint, for example. Information determined or captured by the controller 22 may be transmitted by the communication device 41 to an external device (e.g., a server or to other type of computer) for further analysis and/or display to a user.

It should be noted that the triboelectric sensor 12 is described above as a biosensor capable of measuring body motions by a user. However, the triboelectric sensor 12 may be configured to measure the surface motions of other objects as may be desired.

Now, therefore, the following is claimed:

1. A triboelectric monitoring system, comprising:
   a triboelectric sensor having a first triboelectric element conductively coupled to an electrode, the first triboelectric element having a first layer and a second layer, wherein the first layer has a first surface with first charges dispersed across the first surface, wherein the second layer has a second surface with second charges, including positive and negative charges, dispersed across the second surface, the first layer in contact with the second layer such that electrostatic forces generated by the first charges and second charges hold portions of the first surface and the second surface together and force a plurality of gaps between the first surface and the second surface, wherein stresses applied to the first triboelectric element cause changes in the gaps such that an amount of surface area of the first surface in contact with the second surface changes; and a controller conductively coupled to the electrode, the controller configured to receive and store measurements of a triboelectric voltage generated by the first layer and the second layer in response to the changes in the gaps.

2. The system of claim 1, wherein the controller is configured to analyze the measurements to determine at least one body motion by a user wearing the triboelectric sensor.

3. The system of claim 1, wherein the first triboelectric element comprises a strip of tape having the first layer and the second layer.

4. The system of claim 1, wherein the first layer is polypropylene.

5. The system of claim 4, wherein the second layer is acrylic.

6. The system of claim 1, wherein the triboelectric sensor is secured to a body of a user such that movement of skin of the user induces stresses on the first triboelectric element.

7. The system of claim 6, wherein the triboelectric sensor is secured to the body of the user by a covering that covers the triboelectric sensor.

8. The system of claim 7, wherein the covering comprises tape.

9. The system of claim 1, further comprising a second triboelectric element conductively coupled to the electrode.

10. The system of claim 9, wherein the second triboelectric element has a third layer and a fourth layer, wherein the third layer has a third surface with third charges dispersed across the third surface, wherein the fourth layer has a fourth surface with fourth charges, including positive and negative charges, dispersed across the fourth surface, the third layer in contact with the fourth layer such that electrostatic forces generated by the third charges and fourth charges hold portions of the third surface and the fourth surface together and force a plurality of gaps between the third surface and the fourth surface, wherein stresses applied to the second triboelectric element cause changes in the gaps between the third surface and the fourth surface such that an amount of surface area of the third surface in contact with the fourth surface changes.

11. The system of claim 10, wherein the first triboelectric element comprises a strip of tape having the first layer and the second layer, and wherein the second triboelectric element comprises a strip of tape having the third layer and the fourth layer.

12. A triboelectric monitoring method, comprising:

providing a triboelectric sensor having a first triboelectric element conductively coupled to an electrode, the first triboelectric element having a first layer and a second layer, wherein the first layer has a first surface with first charges dispersed across the first surface, wherein the second layer has a second surface with second charges, including positive and negative charges, dispersed across the second surface, the first layer in contact with the second layer such that electrostatic forces generated by the first charges and second charges hold portions of the first surface and the second surface together and force a plurality of gaps between the first surface and the second surface;

applying stresses to the first triboelectric element, thereby causing changes in the gaps, such that an amount of surface area of the first surface in contact with the second surface changes;

generating a triboelectric voltage with the first layer and the second layer in response to the changes in the gaps;

measuring the triboelectric voltage via the electrode; and storing, in memory, data indicative of the measuring.

13. The method of claim 12, further comprising analyzing the measurements with a controller to determine at least one body motion by a user wearing the triboelectric sensor.

14. The method of claim 12, wherein the first triboelectric element comprises a strip of tape having the first layer and the second layer.

15. The method of claim 12, wherein the first layer is polypropylene.

16. The method of claim 15, wherein the second layer is acrylic.

17. The method of claim 12, further comprising securing the triboelectric sensor to a body of a user, wherein the stresses are in response to movement of skin of the user.

18. The method of claim 17, wherein the securing comprises covering the triboelectric sensor with a cover.

19. The method of claim 18, wherein the covering comprises tape.

20. The method of claim 12, further comprising conductively coupling a second triboelectric element to the electrode.

21. The method of claim 20, wherein the second triboelectric element has a third layer and a fourth layer, wherein the third layer has a third surface with third charges dispersed across the third surface, wherein the fourth layer has a fourth surface with fourth charges, including positive and negative charges, dispersed across the fourth surface, the third layer in contact with the fourth layer such that electrostatic forces generated by the third charges and fourth charges hold portions of the third surface and the fourth surface together and force a plurality of gaps between the third surface and the fourth surface, and wherein the method further comprises applying stresses to the second triboelectric element, thereby causing changes in the gaps between the third surface and the fourth surface, such that an amount of surface area of the third surface in contact with the fourth surface changes.

22. The method of claim 21, wherein the first triboelectric element comprises a strip of tape having the first layer and the second layer, and wherein the second triboelectric element comprises a strip of tape having the third layer and the fourth layer.

* * * * *